United States Patent

Diffenderfer

(10) Patent No.: US 10,748,653 B2
(45) Date of Patent: Aug. 18, 2020

(54) HEALTHCARE PROXIMITY CONTEXTUAL AWARENESS AND NOTIFICATION

(71) Applicant: Cerner Innovation, Inc., Kansas City, KS (US)

(72) Inventor: Aaron Timothy Diffenderfer, Belton, MO (US)

(*) Notice: Subject to any disclaimer, the term of this patent is extended or adjusted under 35 U.S.C. 154(b) by 644 days.

(21) Appl. No.: 14/961,080

(22) Filed: Dec. 7, 2015

(65) Prior Publication Data

US 2017/0109482 A1 Apr. 20, 2017

Related U.S. Application Data

(60) Provisional application No. 62/243,745, filed on Oct. 20, 2015.

(51) Int. Cl.
*G16H 40/20* (2018.01)
*G06Q 10/10* (2012.01)

(52) U.S. Cl.
CPC ............ *G16H 40/20* (2018.01); *G06Q 10/10* (2013.01)

(58) Field of Classification Search
None
See application file for complete search history.

(56) References Cited

U.S. PATENT DOCUMENTS

| | | | |
|---|---|---|---|
| 2005/0021369 A1* | 1/2005 | Cohen | G06Q 30/02 705/2 |
| 2009/0119124 A1* | 5/2009 | Kambaloor | G06Q 50/22 705/2 |
| 2010/0217513 A1* | 8/2010 | Takeda | G01C 21/343 701/532 |
| 2011/0106565 A1* | 5/2011 | Compton | G06Q 50/22 705/3 |
| 2011/0221590 A1* | 9/2011 | Baker | A61B 5/0002 340/539.12 |

* cited by examiner

*Primary Examiner* — Michael Tomaszewski
(74) *Attorney, Agent, or Firm* — Shook, Hardy & Bacon LLP

(57) ABSTRACT

A system and method are provided for notifications and automatic selections based on location proximity. The embodiments of the present invention provide a method and system that are contextually aware of a user's proximity to other subjects, hence providing the user with automatically enhanced and improved healthcare workflow. The embodiments of the present invention are useful for improved workflow and enhanced efficiency in healthcare facilities. The contextual awareness is prescriptively providing users with the necessary information based on their location proximity. The information gathered from proximity may be used to aid in the determination of additional improvements to healthcare workflows.

20 Claims, 8 Drawing Sheets

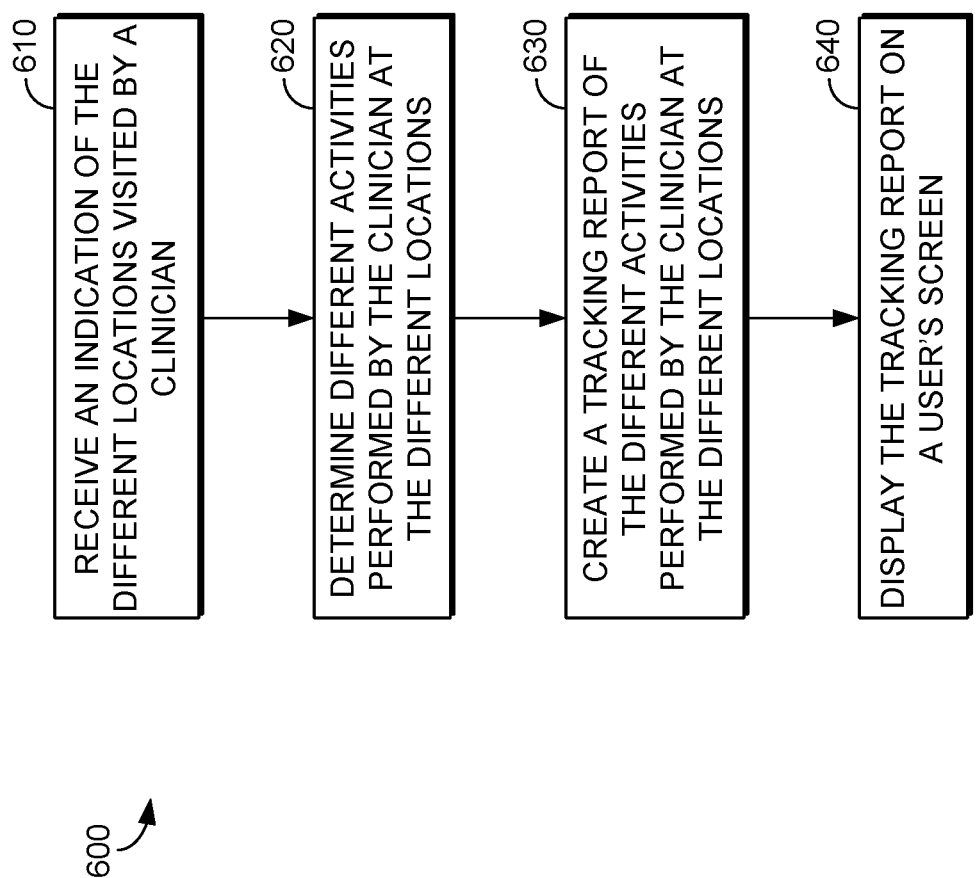

| PATIENT LISTS | | | | | | | | | | |
|---|---|---|---|---|---|---|---|---|---|---|
| 2N | CARDIOLOGY UNIT | ACTIVE PATIENT LISTS OPENED BY MARYLAN MD, JOHN | | | | | | | | |
| CONFIDENTIAL | NAME | ROOM | MRN | FIN | AGE | DOB | GENDER | ADMINISTERING PHYSICIAN | CONSULTING PHYSICIAN | VISIT REASON | LENGTH OF STAY |
| | TEST, MEDSREC2 | 2701 | 02940 | 17637 | 40 YO | 03/25/71 | FEMALE | TEST, PHYSICI... | | | 14.0 DAYS |
| ☆ | TEST, CHEUNG | 2708 | 01120 | 13722 | 30 YO | 06/15/80 | MALE | CHEUNG, FELX... | | LEFT ARM | 165.1 DAYS |
| ☆ | TEST, CHEUNG | 2708 | 01120 | 15016 | 30 YO | 06/15/80 | MALE | CHEUNG, FELX... | | LEFT ARM | 44.2 DAYS |
| | BUILD, TEST | 2709 | 01108 | 13607 | 55 YO | 05/05/55 | MALE | CORN, GEORG... | | TESTING | 170.0 DAYS |
| | TEST, CPOESV | 2702 | 02886 | 16985 | 30 YO | 02/11/81 | MALE | TEST, PHYSICI... | TEST, PHYSICI... | | 43.9 DAYS |
| | TEST, NOVOTY | 2753 | 01150 | 14365 | 61 YO | 01/01/50 | MALE | NOVOTNY, PHY... | | FX | 88.1 DAYS |
| | ZWICKER, MARK | 2757 | 02864 | 16753 | 25 YO | 12/20/85 | MALE | TEST, PHYSICI... | TEST, PHYSICI... | | |
| | TEST, DAY | 2751 | 01121 | 13730 | 41 YO | 02/14/70 | FEMALE | DAY, JAMES | | HAND FX | 165.1 DAYS |
| | TEST, PP2 | 2704 | 02925 | 17488 | 23 YO | 02/18/88 | MALE | TEST, PHYSICI... | | TEST PO... | 18.0 DAYS |
| | TEST, CPOESV | 2705 | 02901 | 17157 | 41 YO | 01/01/70 | MALE | TEST, ED PHYS... | TEST, PHYSICI... | CHEST P... | 38.7 DAYS |
| | TEST, CPOESYS | 2703 | 02885 | 16977 | 41 YO | 01/01/70 | MALE | TEST, PHYSICI... | TEST, PHYSICI... | | 43.9 DAYS |

EXAMPLE, MO... ×  |  NEW STICKY NOTE  VIEW STICKY NOTE  TEAR OFF  ATTACH  SUSPEND  EXIT  CALCULATOR  DEPART

EXAMPLE, MORROS A  AGE: 49 YEARS  SEX: MALE  LOCATION: NW-3B; 0324; 01  LIST  RECENT  NAME
DOB: 7/4/1959  MRN: NW#00002163  FIN NUMBER: 315233

ALLERGIES: AMOXICILLIN

ORDERS  PRINT

+ ADD  DOCUMENT MEDICATION | RECONCILIATION ▼

TASKS | MEDICATION LIST

VIEW
- TASKS FOR SIGNATURE
  - TASKS
    - ☑ ADMIT/DIAGNOSIS
    - ☑ CODE STATUS
    - ☑ PATIENT ALERTS
    - ☑ VITAL SIGNS
    - ☑ ACTIVITY
    - ☐ DIET
    - ☑ PATIENT CARE ORDERS
    - ☐ RESPIRATORY THERAPY
    - ☐ IV SOLUTIONS
    - ☑ MEDICATIONS
    - ☑ LABORATORY
    - ☑ DIAGNOSTIC TESTS
    - ☐ CONSULTS
    - ☐ OTHER
  - RECONCILIATION HISTORY

RELATED RESULTS — 810

DISPLAY: ALL ACTIVE TASKS  ▼  [...]

| | ORDER NAME | STATUS | DETAILS |
|---|---|---|---|
| ⊞ | ADMIT/DIAGNOSIS | | |
| ☑ | ADMIT TO | ORDERED | 10/14/08 10:52:00, INPATIENT, ACUTE CARE/MED... |
| ☑ | ADMITTING PHYSIC... | ORDERED | 10/14/08 10:52:00, RAVI M.D., CHAITAYNA |
| ☑ | DIAGNOSIS | ORDERED | 10/14/08 10:52:00, CAT SCRATCH FEVER |
| ⊞ | CODE STATUS | | |
| ☑ | RESUSCITATION STATUS (CODE STATUS) | ORDERED | 10/14/08 10:52:00, FULL RESUSCITATION |
| ⊞ | PATIENT ALERTS | | |
| ☑ | MED. HISTORY FOLLOW-UP REQUIRED | ORDERED | 10/14/08 11:04:36 THIS ORDER WAS PLACED BY DISCERN EXPERT |
| ☑ | ISOLATION | ORDERED | 10/14/08 10:54:00, CONTACT |
| ⊞ | VITAL SIGNS | | |
| ☑ 66 | VITAL SIGNS | ORDERED | 10/16/08 10:26:00, Q4H |
| ⊞ | ACTIVITY | | |
| ☑ | OUT OF BED (OOB) | ORDERED | 10/14/08 10:54:00, AS TOLERATED |
| ◢ | DETAILS | | |

DISPLAYED: ALL ACTIVE ORDERS

CUSTOM — 820

800

HEALTHCARE PROXIMITY CONTEXTUAL AWARENESS AND NOTIFICATION

CROSS-REFERENCE TO RELATED APPLICATIONS

This application claims priority to U.S. Provisional Application No. 62/243,745, filed Oct. 20, 2015, entitled "Healthcare Proximity Contextual Awareness and Notification," the entire contents of which are herein incorporated by reference.

BACKGROUND

Workflow in healthcare systems includes a series of tasks of clinical services that determines by whom different tasks are accomplished, in which order, and to whom they are given. The quality of care in hospitals depends on the efficiency of the clinicians' workflows. Efficient workflows are critical for clinical outcomes and for the care of patients. Inefficient clinical workflows may result in longer wait times for patients and more hours wasted by clinicians in unnecessary efforts.

With the wide use of technology in healthcare systems, new technologies should emerge to support a more efficient and improved clinical workflow. Unnecessary communication between healthcare personnel and needless activities performed by clinicians may lead, in many cases, to inefficient clinical workflows due to interruptions or miscommunications among clinicians. New technologies are needed to help clinicians have more efficient workflows that lead to a higher quality of patient care.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

The claimed invention relates to a system and method supporting computerized healthcare information systems. More specifically, the claimed invention relates to a system and method for computer-based healthcare information users to have enhanced healthcare workflows based on contextual awareness.

The claimed solution is necessarily rooted in computerized healthcare workflow of clinicians in order to overcome a problem specifically arising in the realm of computer healthcare information networks, and the claims address the problem of efficiently handling the workflow of clinicians through proximity contextual awareness. If adhering to the routine and conventional methods of assigning and managing workflows in a healthcare information system, clinicians and other users have to click multiple times and perform manual steps to obtain information such as selecting a patient list, looking up patient information, and keeping track of time frames for patient activities. Healthcare associates may forget to perform various actions during their day. This can cause delays and allow incorrect information to be entered, and may lead to inefficient workflows.

The claimed invention overcomes the limitations of current computer healthcare information technology and provides other benefits that will become clear to those skilled in the art from the foregoing description.

The claimed system and method of the present application represents a new paradigm of providing improved workflow with an enhanced efficiency. Not only does the claimed invention provide clinicians with an enhanced and efficient workflow without manual entry, but it also prevents errors in entry of the information and saves the clinician time, which could be used for patient care. Users of the claimed invention will notice improved performance of their workflow, increased retrieval of different information, fewer user steps to build or utilize workflows, and user access to different information. Furthermore, anything that reduces the number of "clicks" or entries a computer user has to make in an Electronic Medical Record (EMR), or Electronic Health Record (EHR) or healthcare workflows, results in reducing the memory utilization, CPU cycles, number of operations that need to be performed by the computer, and power consumption. The resulting cost savings and operational efficiencies of a computer in handling clinicians' workflows magnify the potential benefits of this technology.

Embodiments of the present invention provide a system and method so healthcare associates will no longer have to take unnecessary steps in their workflows in a healthcare system. Their devices will be contextually aware with regard to location proximity and make the appropriate determination for them, providing them with necessary and relevant information at the time that it is needed.

One embodiment of the present invention is directed to a set of computer-useable instructions providing a method for enhancing healthcare workflows based on proximity. The location of a clinician is received by way of a clinician identifier that is tracked via a sensor in a healthcare environment. A determination is made of the patients that relate to the clinician within a specified range of the clinician's location. The determination is based on the proximity of the sensors that identified the location of both the clinician and the patients. Based upon a determination that the location for the clinician and the location of the patients are within a specified range, the patients' charts or other relevant information are automatically loaded to the clinician's device.

In another embodiment, a set of computer-useable instructions providing a method for enhancing healthcare workflows based on location proximity is provided. An indication is received to specify the location of a clinician in a healthcare facility. The location of the clinician is received by way of a clinician identifier that is tracked via a sensor in a healthcare environment. A determination is made of the different patients that relate to the clinician's specialty within a specified range. The determination is based on the proximity of the sensors that identified the locations of different patients and the clinician. Upon determining that the locations of different patients are within a specified range of the clinician's location, a patients list is built, populated, and loaded to the clinician's device.

In another embodiment, a set of computer-useable instructions providing a method for enhancing healthcare workflows based on location proximity is provided. An indication is received of the different locations visited by a clinician within a specified range of time. The location of the clinician is received by way of a clinician identifier that is tracked via a sensor in a healthcare environment. A determination is made of the different patients that were visited or not by the clinician. The determination is based on the proximity of the sensors that identified the locations of the different patients and the clinician to be within a specified range. Upon determining the locations of different patients visited by the clinician, a tracking report of the clinician's activities within the specified range of time is created.

In yet another embodiment, a handheld computing device for enhancing healthcare workflows based on location proximity is provided. The handheld computing device includes one or more graphical user interfaces for displaying location information, including displaying nearby patients in location proximity with the user within a specified range. The handheld computing device includes a determination component for determining if different subjects are in proximity of a specified range from the location of the user. The handheld computing device also includes an extraction communication component for filtering the subjects list inside the facility based on their location within a specified range in location proximity to the user and extracting different charts or relevant information for the filtered subjects list. The handheld computing device also includes one or more graphical user interfaces for displaying patients' charts, patients lists, tracking reports, and clinician information, including notifying a user of clinical events and displaying alerts to a plurality of users.

Additional objects, advantages, and novel features of the invention will be set forth in part in the description which follows, and in part will become apparent to those skilled in the art upon examination of the following, or may be learned by practice of the invention.

BRIEF DESCRIPTION OF THE DRAWINGS

Embodiments are described in detail below with reference to the attached drawing figures, wherein:

FIG. 6 depicts a flow diagram illustrating a third exemplary method for determining location proximity to enhance and improve healthcare workflows, in accordance with embodiments of the present invention; and FIG. 7 depicts an illustrative graphical user interface displaying a patients list and other relevant information in a healthcare facility, in accordance with an embodiment of the invention.

FIG. 8 depicts an illustrative graphical user interface displaying a task list associated with a patient in proximity with the clinician in a healthcare facility, in accordance with an embodiment of the invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Some embodiments are described herein in terms of proximity and contextual awareness and notification systems, such as might be used in any facility or maybe any other clinical setting. However, some embodiments of the invention are not limited to any particular type of medical proximity and contextual awareness and notification systems, nor are they limited to medical applications in general. An embodiment may provide contextual help to users of other, non-medically related types of applications.

Embodiments may be embodied as, among other things: a method, system, or set of instructions embodied on one or more computer-readable media. Computer-readable media include media implemented for storing information. Examples of stored information include computer-useable instructions, data structures, program modules, and other data representations. By way of example, and not limitation, computer-readable media may comprise computer storage media. Computer-readable media include both volatile and nonvolatile media, removable and non-removable media, and contemplate media readable by a database, a switch, and various other network devices. Media examples include hardware memory devices such as RAM, ROM, EEPROM, flash memory or other memory technology, CD-ROM, digital versatile disks (DVDs), holographic media or other optical disk storage, magnetic cassettes, magnetic tape, magnetic disk storage, and other data storage devices. These technologies can store data momentarily, temporarily, or permanently. As used herein, computer-readable media do not include signals per se.

Figure 1:
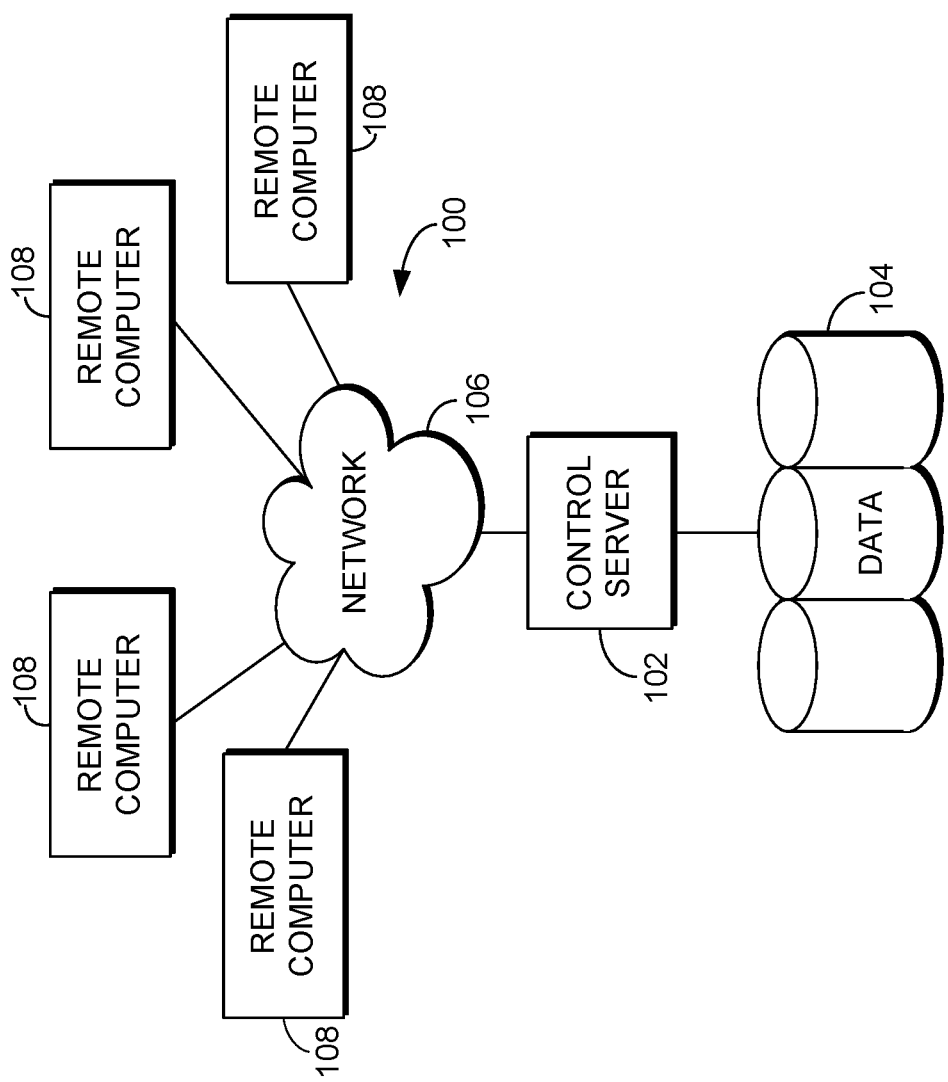
FIG. 1 depicts a block diagram of an illustrative operating environment suitable for practicing the present invention.

Referring now to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

Embodiments of the present invention may be operational with numerous other general-purpose or special-purpose computing system environments or configurations. Examples of well-known computing systems, environments, and/or configurations that may be suitable for use with the present invention include, by way of example only, personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general-purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer-readable media, for instance, database cluster 104. Computer-readable media can be any available media that may be accessed by server 102, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Communication media typically embodies computer-readable instructions, data structures, program modules, or other data in a modulated data signal, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home healthcare environments, and clinicians' offices. Clinicians may include, but are not limited to, a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. The remote computers 108 may also be physically located in non-traditional medical care environments so that the entire healthcare community may be capable of integration on the network. The remote computers 108 may be personal computers, servers, routers, network PCs, mobile phones, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnections are well known. Accordingly, additional details concerning the internal construction of the server 102 and the remote computers 108 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare orders. As contemplated by the language above, the methods and systems of embodiments of the present invention may also be implemented on a stand-alone desktop, personal computer, or any other computing device used in a healthcare environment or any of a number of other locations.

In accordance with embodiments of the present invention, notifications and automatic selections to improve healthcare workflows for clinicians may occur based on location proximity using a computing device, such as exemplary remote computer 108 illustrated in FIG. 1. The computing device may be any device that is capable of creating notifications and automatic selections based on location proximity. Accordingly, the computing device may take on a variety of forms, such as a laptop computer, a mobile phone, a personal digital assistant (PDA), a server, or any other device that is capable of receiving and/or presenting healthcare orders.

As previously mentioned, the present invention is related to improving healthcare workflows based on identifying location proximity among healthcare clinicians and patients to enhance and greatly improve healthcare workflows in a healthcare facility, wherein notifications and automatic selections will occur based on location proximity. The primary benefits with this invention are the improved workflow and enhanced efficiency in a healthcare facility. Users do not have to take unnecessary actions that impede their processes. The contextual awareness will prescriptively provide them the necessary information based on their location proximity. The information gathered from the location proximity can then be used to aid in the determination of additional improvements.

To find the location of a certain user in a facility, various terms are used throughout this description. A full definition of any term can only be gleaned by giving consideration to the full breadth of this document. The term "location" is identified as each unique point of interest in the facility. Each unique point of interest in the facility is identified as a location, e.g., location of clinician. There are two types of locations: a normal location and a junction point. Normal location is a location that is present on a single path and not at the intersection of two paths. While a junction point may or may not be a point of interest in the facility, it is, however, a location in the facility where two paths intersect. It should be identified in the database as a point of interest or not. If the junction point is not a point of interest, it is used only for administration purposes. Another definition is the "path," which is identified as a set of locations connected to each other, which the user can navigate to get from one location to another. Another definition is the "direction," which identifies each individual location in a path. Direction determines the direction to be taken to get to the next location in the path (e.g., North, South, etc.) and the order of the location in the path. Order is an integer, which can start at any end of the path. First location in the path will have order 1. And the number keeps increasing by the count of 1 for each location. For each path, the order value resets.

Different tables are created within the database to identify the location of different users by the embodiments of the present invention. Table 1 is a Path-type lookup table, which contains the different types of paths. There are two types of paths: a common path and a sub path.

TABLE 1

| Column Name | Description |
| --- | --- |
| pathtypeid | Primary key |
| Pathtype | The name of different types of paths |

Table 2 is a lookup table that contains the different types of locations. There two types of locations: general location which identifies points of interest, and junction points which identify points which may or may not be of interest but are used to identify the locations where two paths merge.

TABLE 2

| Column Name | Description |
| --- | --- |
| locationtypeid | Primary key |
| locationtype | The name of different types of locations |

Table 3 shows a table of Location Names, which contains all the location names and location types.

TABLE 3

| Column Name | Description |
| --- | --- |
| locationnameid | Primary key |
| Locationname | The name of the point of interest |
| Locationtypeid | Foreign key reference to location type table (General location, junction point) |

Table 4 identifies a Map table, which contains the URLs to the map images for various floors.

TABLE 4

| Column Name | Description |
| --- | --- |
| Mapid | Primary key |
| mapName | Name of the map (e.g., First floor map, second floor map, etc.) |
| Mapurl | The URL where the map image is uploaded. |
| Floor | The floor of the map. |

Table 5 contains the various paths in the map.

TABLE 5

| Column Name | Description |
| --- | --- |
| Pathid | Primary key |
| Pathname | The name of different paths (e.g., First floor common path, First floor sub path etc.) |
| Pathtypeid | Foreign key reference to path type table (common path, sub path) |
| Mapid | Foreign key reference to map table. This can be used to obtain the floor in which the path is located. |

Table 6 contains the x and y coordinates of a location on the map image.

TABLE 6

| Column Name | Description |
| --- | --- |
| locationid | Primary key |
| Locationnameid | Foreign key reference to locationnames table |
| Mapid | Foregin key reference to Map table |
| Mapxcord | The X-coordinate on the map image |
| Mapycord | The Y-coordinate on the map image |

Table 7 contains the various locations that comprise a path and the directions to be taken to navigate between the locations.

TABLE 7

| Column Name | Description |
|---|---|
| directionid | Primary key |
| pathid | Foreign key reference to path table |
| ord | Contains the order of the location in the path. (e.g., In a path from Location A to Location D which passes through Location C and Location D, Location A takes order 1, Location B takes order 2, Location C takes order 3 and Location D takes order 4). |
| direction | The direction to be taken to navigate from one location to another (North, South, East, West) |
| locationId | Foreign key to location table. |

Once a database is built, the embodiments of the present invention include creating a data structure similar to a tree structure. This data structure will have information about each junction point. This is typically created as Java class, e.g., consider this class as JunctionPoint. If there are multiple sub paths passing through a given junction point, then multiple JunctionPoint instances are created for that junction point, one per path. Table 8 shows a list of different fields present in JunctionPoint.

TABLE 8

| Field | Type | Description |
|---|---|---|
| locationId | Int | Contains the location Id of the current junction point |
| pathId | Int | Contains the path ID passing through that junction point. If there are multiple paths that pass through a given junction point, multiple instances of the JunctionPoint class will have to be created, one per pathId.<br>It is to be noted that only sub paths should be considered as paths passing through a junction point. Common paths should be neglected. |
| allChildren | Set<Integer> | All the child locations under this junction point, in other words all the points of interest and other junction points in order to get to which we will have to pass through the junction point are included under allChildren. |
| directChildren | Set<Integer> | The points of interest and other junction points which are directly under the junction point under consideration are called directChildren. In other words, all the points of interest and junction points which exist on the path defined by the pathId (mentioned above) are called direct children. In other words, from the junction point under consideration, the locations to which a user can get to without taking a detour at any other junction point is considered to be a direct child. |
| Parent | JunctionPoint | In simple terms, parent is a junction point which is hierarchically the parent of the current junction point.<br>For example, in the figure defined above: There are 3 junction points with location id 6, 8, and 9.<br>JunctionPoint - 6: This junction point exits on the common path. So it doesn't have any parent.<br>JunctionPoint - 8: The parent is 6. This is because in order to get to junction point 8, one has to go through 6.<br>JunctioPoint - 9: The parent of 9 is also 6. Though in order to get to 9, one has to pass through 8, 8 is still not considered the |

TABLE 8-continued

| Field | Type | Description |
|---|---|---|
| junctionPoints | Set<JunctionPoint> | parent of 9 because 8 and 9 are on the same path, which means they are at the same level. All the child junction points are again constructed into individual objects and created as a set of JunctionPoints and stored in the parent. |

Figure 2:
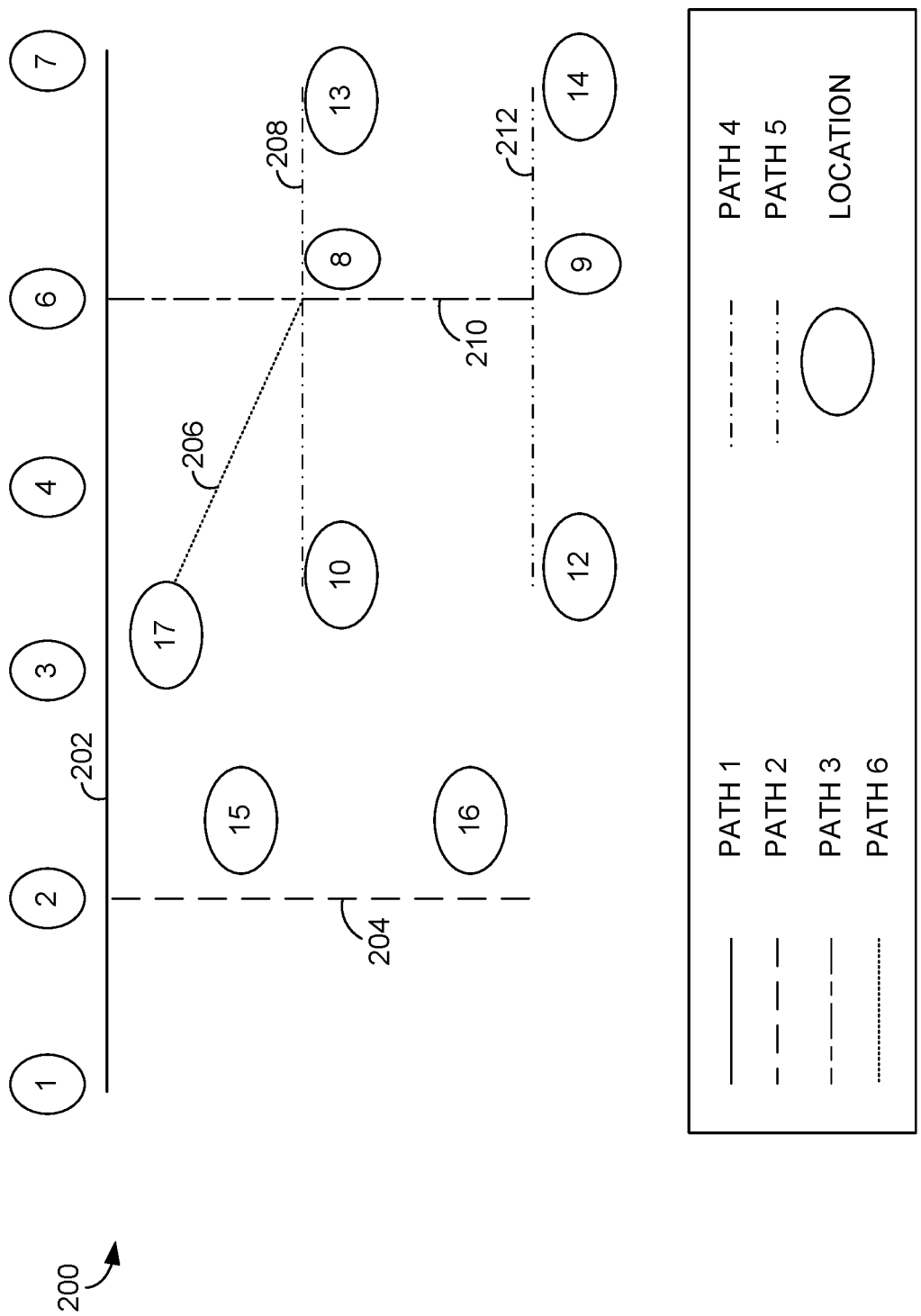
FIG. 2 depicts a layout diagram illustrating the different paths exemplified in the present invention for finding locations on the same floor, in accordance with embodiments of the present invention.

Turning now to FIG. 2, an illustrative layout diagram for finding locations on the same floor is provided. In FIG. 2, path 1 is the common path 202. Paths 2 204, path 3 210, path 4 208, path 5 212, and path 6 206 are the side paths. Locations 2, 6, 8, and 9 are the junction points. If there are multiple sub paths passing through a given junction point, then multiple JunctionPoint instances are created for that junction point, one per path. For example, using the layout of FIG. 2, the data structure of the junction point at location id-6 will be:
 1) locationId-6.
 2) pathId—There is only one path through the location (pathid=3). It is to be noted that common paths are not considered in this process.
 3) allChildren—In order to reach location ids 8, 9, 10, 11, 12, 13, 14, and 16, we have to pass through 6. There is no way to reach any of these locations without passing through 6.
 4) directChildren—8 and 9.
 5) Parent—Junction point 6 is also on the common path. So we did not have to pass through a junction point to reach junction point 6. So there is no parent for junction point 6. This will be explained using another junction point.

Still at FIG. 2, another example as in the case of junction point at location id-8, there are multiple sub paths passing through it (Path 4 and Path 6). Two instances of the JunctionPoint class have to be created. One instance should have pathId as 4 and the child points should be the ones along that path, and another instance with pathId as 6 with child points along path 6.

It is to be noted that the path that has already been covered as a part of another junction point should be avoided. This is why, though pathId 3 passes through junctionPoint-8, since it was already covered as a part of JunctionPoint-6, it is neglected.
 Instance 1:
 1) locationId=8
 2) pathId=4
 3) allChildren=10, 13, 17
 4) directChildren=10,13
 5) Parent=6
 Instance 2:
 1) locationId=8
 2) pathId=6
 3) allChildren=10, 13, 17
 4) directChildren=17
For junction point at location id-9, there is only one path through this junctionPoint. PathId=5.
 1) locationId=9
 2) pathId=5
 3) allChildren=12,14
 4) directChildren=12,14
 5) Parent=6

Another example is the junction point at location id-2, where there is only one path through this junctionPoint. PathId=2.
 1) locationId=2
 2) pathId=2
 3) allChildren=15,16
 4) directChildren=15,16
 5) Parent=null.

The embodiments of the present invention include a method of constructing a data structure using a recurring call. In order to reduce the complexity and to improve modularity, the recurring calls are handled inside the data structure through the following steps:

Step 1: All the junction points on the common path are fetched.

Step 2: The junction points are iterated, and the sub paths through each junction point are fetched.

Step 3: The list of locations (junction points and points of interest) on each path are fetched and added to the direct children by calling the addDirectChildren method in the JunctionPoint class.

Step 4: The addDirectChildren method in turn calls the addAllChildren method. This is based on the logic that elements in a direct children list always belong to the all children list. But the elements in the all children list may or may not belong to the direct children list.

Step 5: The addAllChildren method in turn calls the addAllChildren method of the parent. This is based on the logic that if a location is in the direct children list of the child, then it should be in the all children list of the parent, and it cannot be in the direct children list of the parent.

Step 6: Steps 1 to 5 are repeated for all the location ids in the all children list of every child location id.

Step 7: All the common junction points constructed as mentioned above are grouped per floor and are added to a hash map, which takes the floor number as the key and Set of Junction points as the value.

At this stage, a data structure is constructed which can help to reach a junction point on the common path. If the required location id is present in the allChildren list of a junction point, it means either this junction point has the location id or one of its children has the location id for the required location id. If the required location id is present in the directChildren list of a junction point, it means that the nearest junction point to the location id is the current junction point.

In the method of the present invention, when both the source and destination are present on the same floor, then there are different cases as follows:
 1) Source is on the common path and destination is on the sub path.
 2) Destination is on the common path and source is on the sub path.

3) Source and destination are on the sub paths, but under different common junction points (junction point on the common path).

4) Source and destination are on the common path.

5) Source and destination are on the sub paths but under the same common junction point.

For cases 1 to 3, it's essential to find the way to reach the common junction point. The method of the present invention will find the path to reach the common junction point as follows:

a) Find the junction point on the common path that has the destination location id in all children.

b) Check if it is in the direct children of that junction point.

c) If it is present, then the common junction point is the nearest junction point.

d) Else, find the child junction point that has the destination location id in all children.

e) Similarly, check if it is also in direct children.

f) Repeat this operation until the junction point which has the location id in direct children is identified.

In more detail, in case 1 where the source is on the common path and destination is on the sub path, the path from destination to the common junction point is identified. The path from the source (which is on the common path) to the common junction point is identified. Both these paths are combined to get the full path from source to destination.

With regard to case 2, the path from source (which is on sub path) to the common junction point is identified. The path from the destination (which is on the common path) to the common junction point is identified.

In view of case 3, the path from source to common junction point of source is identified. The path from destination to common junction point of destination is identified. The path from common junction point of source to the common junction point of destination is identified. All 3 clusters are combined together to get the path from source to destination.

When the source and destination are on the common path as in case 4, which is the simplest of the cases, the path from source to destination is the common path.

In case 5, when the source and destination are on sub paths and if both of them are under the same common junction point, then it essentially means that both the points are under the same island (for example, navigating from Location 13 to Location 14 in FIG. 2). So some of the junction points to pass through to get to the source and the junction points to pass through to get to destination might overlap. In order to get to the destination from the source, one has to really get to the last junction point that is common between source and destination in their list of junction points to get to the common junction point. So the path can be obtained by combining the path from source to last common junction and from last common junction point to destination.

Other methods need distance between various points to compute the shortest distance. In an indoor facility, with a finite number of possible paths, distance might not be required to calculate the shortest distance. Even if a longer path is obtained, the difference in distance between the shortest possible path and long path would be negligible. The embodiments of the present invention do not use distances, and it would also give the shortest possible path in most cases. In other methods, all the neighboring points and various possible routes are analyzed to arrive at the shortest possible path. Whereas in embodiments of the present invention, basic paths are already defined. All that has to be done while finding the path from source to destination is to join individual path segments thereby making it faster.

Moreover, proximity determined in one embodiment in the present invention as the shortest or best possible path as described above with reference to FIG. 2, and not the shortest distance, between a clinician and a patient. For example, in FIG. 2, a clinician at location 3 has a shorter distance, compared to another clinician at location 6, as the shortest distance between the clinician location 3 and the patient location 17. However, the embodiments of the present invention would determine that the clinician at location 6 is in proximity to the patient at location 17 as it has a shorter path. It will be appreciated while one exemplary method of determining that determination of the shortest or best possible path is but one way of determining proximity between a clinician and a patient. For example, in some embodiments, proximity may be determined as the shortest actual distance between the clinician and a patient.

Figure 3:
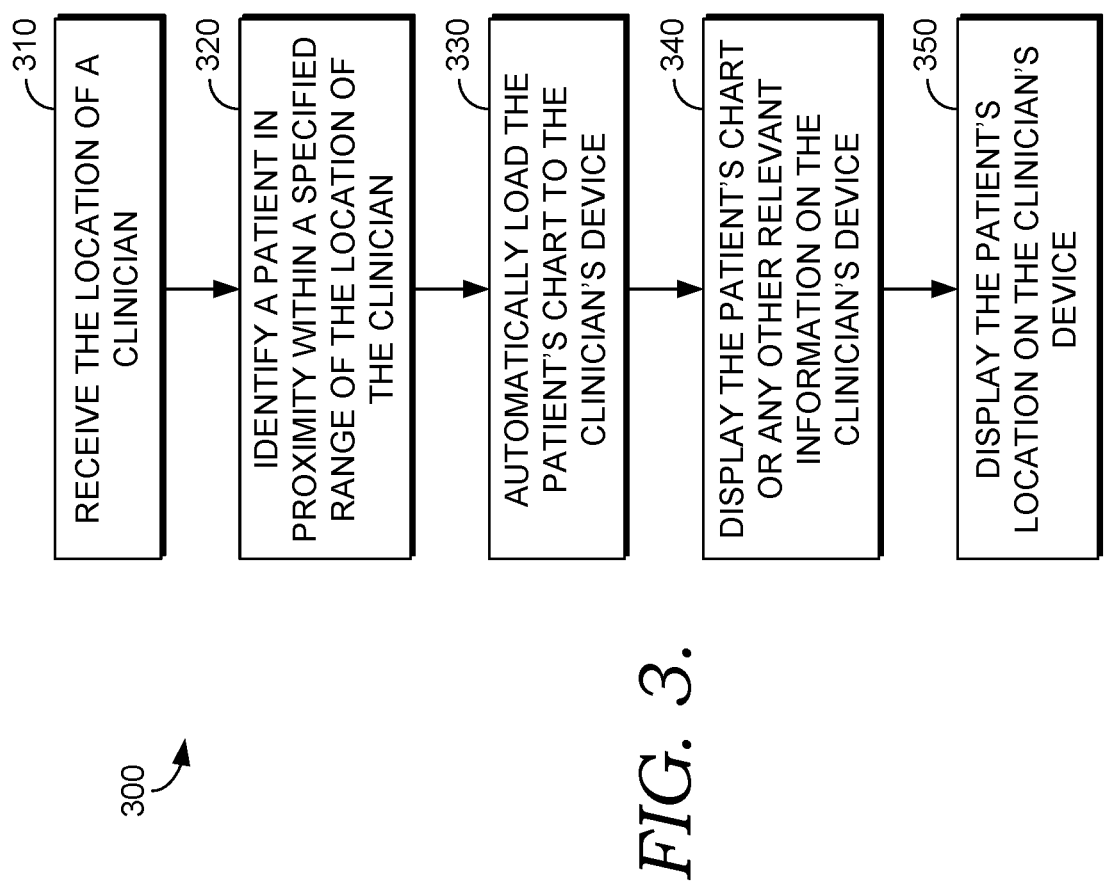
FIG. 3 depicts a flow diagram illustrating a first exemplary method for determining location proximity to enhance and improve healthcare workflows, in accordance with embodiments of the present invention.

Turning now to FIG. 3, a first exemplary method 300 for enhancing healthcare workflows based on proximity is provided. At block 310, the location of a clinician (e.g., doctor, nurse, etc.) is received. Clinician location information is monitored via clinician identifiers. Clinician identifiers may take the form of a security badge, an item attached to a security badge, or the like. The clinician identifiers are tracked by way of sensors located in the healthcare environment. The sensors may utilize ultrasound technology, infrared technology, radio-frequency identification (RFID) technology, or the like. Using said technology, the sensors send out signals to identifiers. An exemplary sensor system is the Cricket Indoor Location System sponsored by the MIT Project Oxygen partnership.

The signals are received by the identifiers and the identifiers respond to the signals. A response from an identifier is received by the sensors and the sensors are able to recognize and determine the location of the responding identifier. When a clinician identifier is identified by a sensor, the location for the clinician associated with the clinician identifier is updated.

A patient that is in proximity, for example, has the shortest possible path to the clinician, and located within a specified range from the clinician is identified at block 320. A determination is made whether the location for the clinician and the location for the patient are near one another or within a specified range. The determination is based on the proximity of the sensors that identified the location of both the clinician and the patient. For example, the location of the sensors may be presented on the computing device via a blueprint of the healthcare environment. If the clinician and the patient are identified by a sensor, their respective locations will be presented on the computing device. The computing device may access the actual location of the sensors within the healthcare environment and the distance between the sensors. Thus, the computing device is able to identify the sensors associated with the respective locations of the clinician and the patient and determine whether they are near one another or within a specified range of proximity. The phrase "near one another or within a specified range," as used herein, generally refers to a predefined proximity between the clinician and the patient or any other individual and/or item associated with an identifier. A user may define "near one another" or "within a specified range" to be any variable that is appropriate for their use. For instance, a user may define being near one another or within a specified range as being on the same floor of a healthcare facility, while another user may define being near one another as being on the same wing of a healthcare facility. Further examples of being near one another or within a specified range may include actual distance, e.g., 200 feet from one another.

Upon determining that the location for the clinician and the location for the patient are within a specified range, the patient's chart or any other relevant information is automatically uploaded to the clinician's computing device at block 330. At block 340, the patient's chart is displayed to the clinician on the computing device. At block 350, the patient's location is displayed to the clinician on the computing device.

Figure 4:
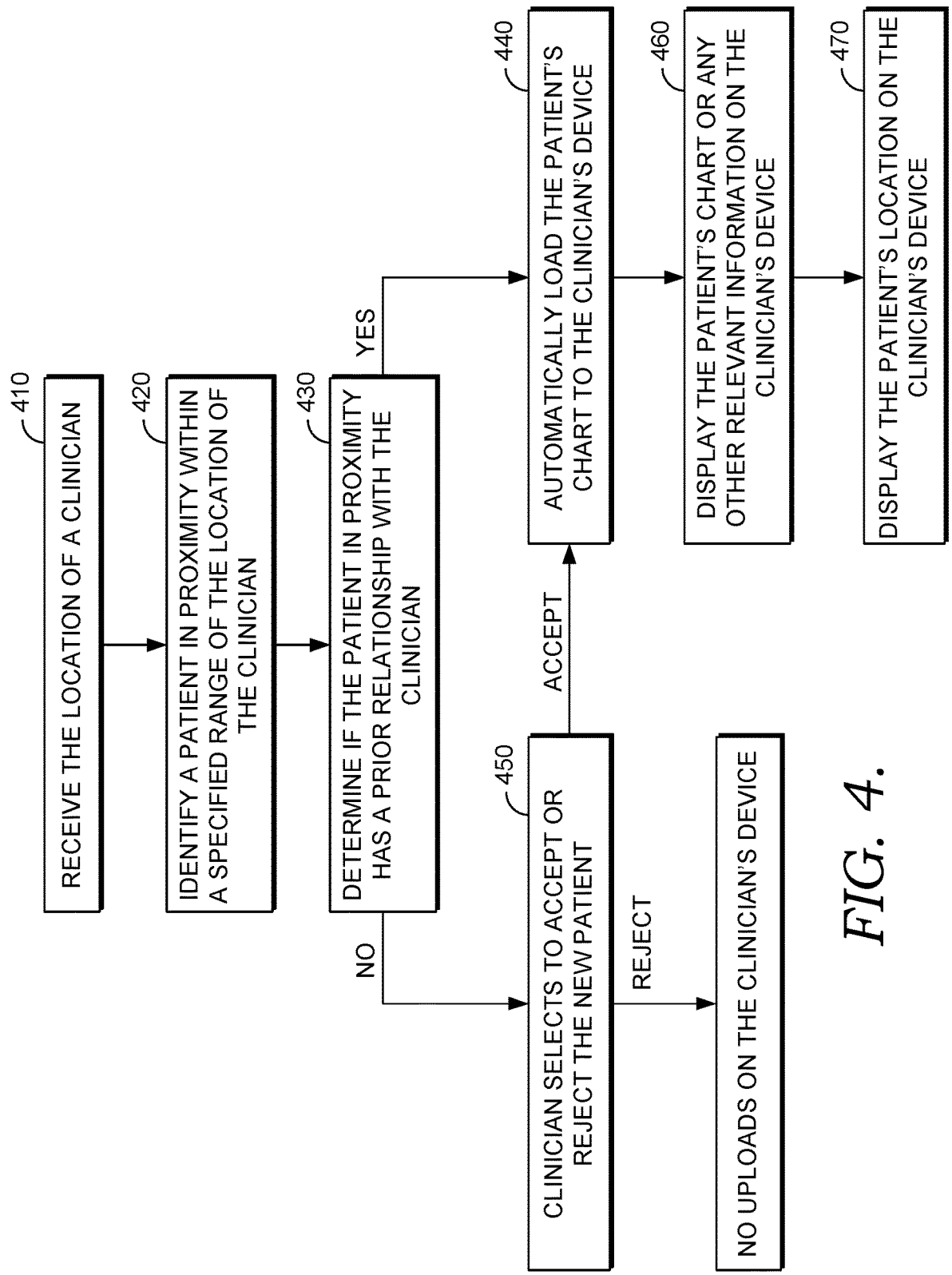
FIG. 4 depicts a flow diagram illustrating a second exemplary method for determining location proximity to enhance and improve healthcare workflows, in accordance with embodiments of the present invention.

Turning now to FIG. 4, a second exemplary method 400 for enhancing healthcare workflows based on proximity is provided. At block 410, the location of a clinician (e.g., doctor, nurse, etc.) is received. Clinician location information is monitored via clinician identifiers. The clinician identifiers are tracked by way of sensors located in the healthcare environment. A patient that is in proximity, for example the shortest possible path to the clinician, and located within a specified range from the clinician is identified at block 420. A determination is made whether the location for the clinician and the location for the patient are near one another or within a specified range. The determination is based on the proximity of the sensors that identified the location of both the clinician and the patient.

At block 430, upon determining that the location for the clinician and the location for the patient are within a specified range, the system determines if a prior relationship exists between the clinician and the patient in proximity. If a prior relationship is determined between the clinician and the patient in proximity, the patient's chart or any other relevant information is automatically uploaded to the clinician's computing device at block 440. At block 450, if no prior relationship between the clinician and the patient in proximity exists, then the clinician may select to accept or reject that the patient in proximity to be added to his device. If the clinician selects to accept the new patient, then the patient's chart or any other relevant information is automatically uploaded to the clinician's computing device at block 440. At block 480, if the clinician selects to reject the addition of the new patient, the system will not upload the patient's chart or any other relevant information to the clinician's device. At block 460, the patient's chart is displayed to the clinician on the computing device. At block 470, the patient's location is displayed to the clinician on the computing device.

Figure 5:
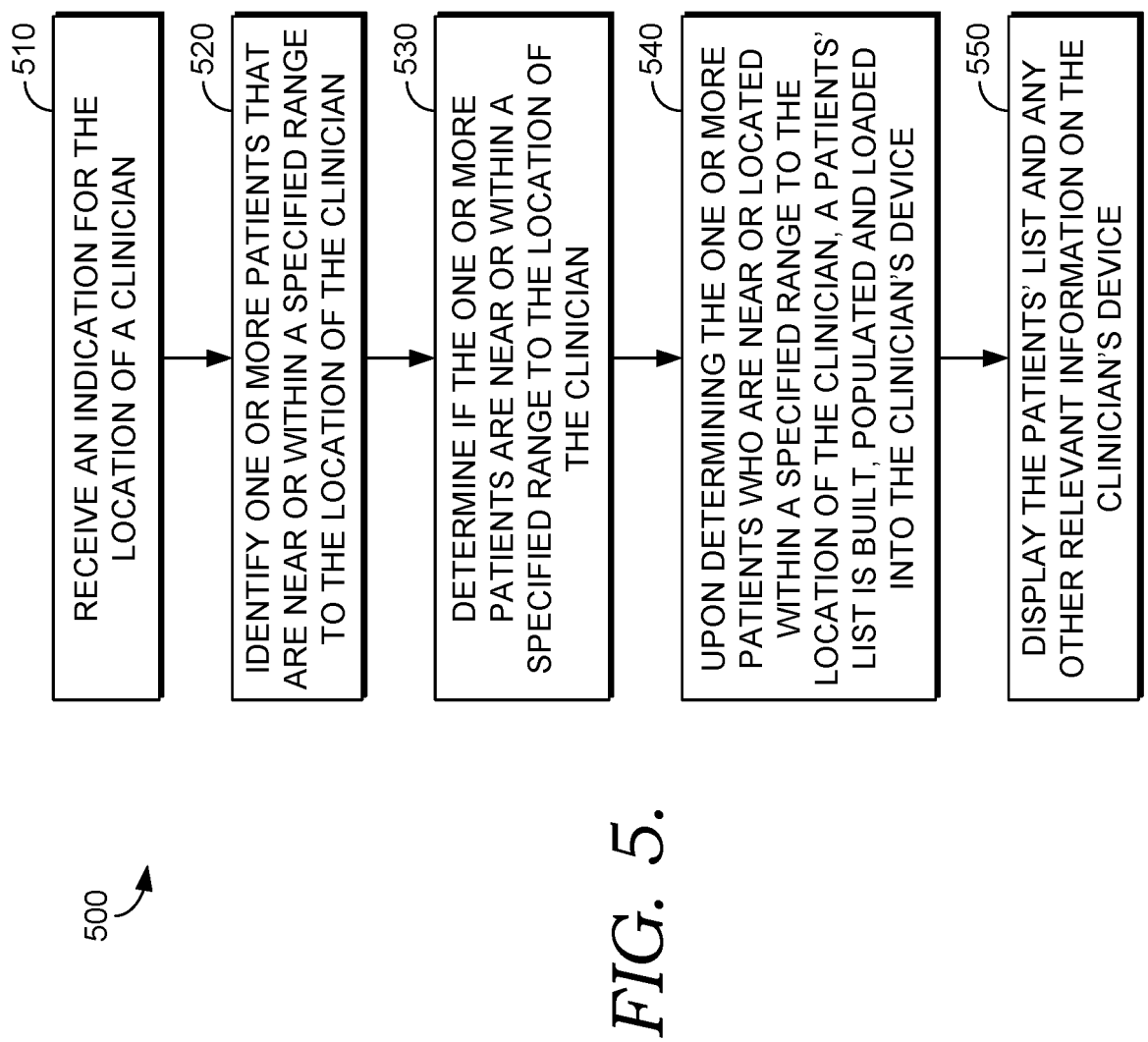
FIG. 5 depicts a flow diagram illustrating a second exemplary method for determining location proximity to enhance and improve healthcare workflows, in accordance with embodiments of the present invention.

With reference to FIG. 5, a third exemplary method 500 for enhancing healthcare workflows based on proximity is provided. An indication for the location of a clinician is received at block 510. At block 520, one or more patients who are near or within a specified range to the clinician's location are identified. The clinicians and the one or more patients are both tracked via a clinician identifier and/or a patient identifier, respectively. At block 530, a determination is made if the one or more patients are near or within a specified range to the clinician's location. Upon determining that the one or more patients are near or within a specified range to the clinician's location, a patients list is created, populated, and loaded to the clinician's device at block 540. At block 550, the patients list and any other relevant information are displayed on the clinician's device.

By way of example only, assume that a clinician has a round on the third floor; a clinician's patient list will be selected based on the clinician's location. The clinician's patient list is built and populated as the clinician visits the patients' rooms/beds, e.g., during shift handoff. Clinicians will be prompted to establish a relationship with the patient upon obtaining close proximity, and the clinician's patient list is filtered based on the clinician's location in the hospital, i.e., which floor/unit. The clinician will also be reminded of activities based on location and proximity, e.g., if a nurse is near a medication-dispensing device, the nurse is reminded of medications to obtain for upcoming use. Users, e.g., clinicians, will receive notification reminders of isolation and contact precautions for patients based on their proximity to the patient's room/bed.

Referring now to FIG. 6, a fourth exemplary method 600 for determining location proximity to enhance and improve healthcare workflows is illustrated. Initially, at block 610, an indication of the different locations visited by a clinician is received. At block 620, the different activities performed by the clinician at those different locations, e.g., how many times the clinician visited a patient, are determined. At block 630, a tracking report is created of all the activities performed by the clinicians within a specified range of time at different locations within a healthcare facility. At block 640, the tracking report is displayed on a user's screen. The tracking report may be beneficial in finding ways by different medical managers or directors to improve the clinicians' processes and remove work hindrances.

Referring now to FIG. 7, a graphical user interface 700 of a displayed patients list is illustrated. A list of patients 710 that are in a specified range of the clinician's location is displayed to the clinician as in the exemplary method illustrated in FIG. 5. Other relevant information 720 about each patient is displayed. The patients list organizes patient charts in a way that is useful for healthcare workflow. A patient chart can be opened directly from a patient list 710.

Referring now to FIG. 8, a graphical user interface 800 of a displayed task list associated with a patient is illustrated. Once the clinician has a list of patients that are in a specified range of the clinician's location uploaded and displayed on his device, the clinician can display a task list associated with each patient on the patients list. For each patient in proximity with the clinician, different categories 810 of the task list are displayed on the clinician's device and the details and the status of each task 820 can also be displayed if selected by the clinician.

In addition to the above-described embodiments, the computing device utilized for the present invention may perform other functions to optimize the clinical experience. Navigational directions of a healthcare environment are accessible to a user, and points of interest and directions thereto may also be identified and presented on the computing device. Additional functions by the present invention, to enhance and improve healthcare workflows, could be to propose possible relations without any active data entry. For example, a specialist spends 10 minutes at a patient's bedside, so likely a consult has occurred. Another example, if a resident is in close proximity to an attending medical doctor through morning rounds, then these two have a "relationship" and this attending medical doctor might be a good choice if the resident needs assistance with a patient case later.

Another example, using the ability to determine a clinician's location at a given time, a surgeon who moves to a non-sterile area, e.g., cafeteria, may now be available for a phone call. If an attending medical doctor is at the nurse station, then this attending medical doctor may be the best person to message with a question about a patient. In another example, an out-patient may have a location tracking device during hospital admission, e.g., armband, to facilitate patient-provider relations.

As can be understood, the present invention provides computer storage media, systems, and methods for providing clinical information to clinicians. Embodiments of the present invention may also provide computer storage media, systems, and methods for optimizing a clinical experience.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more computer storage media having computer-useable instructions embodied thereon that, when used by one or more computing devices, cause the one or more computing devices to perform a method for enhancing healthcare workflows based on pathway-proximity, the method comprising:

receiving a clinician location by way of a clinician identifier, wherein the clinician identifier is tracked via a plurality of sensors in a healthcare environment;

based on the receiving, generating a data structure comprising:

a plurality of paths comprising at least two sub paths and a common path, wherein the plurality of paths are associated with the clinician location and a patient location; and a plurality of locations comprising the clinician location, the patient location, and junction points having at least one all child location and at least one direct child location that is relative to a respective sub path, wherein the junction points are locations where at least two of the plurality paths intersect;

comparing, via sending one or more programmatic calls to the data structure, the plurality of paths between the clinician identifier and the patient location;

based at least on the comparing, automatically determining if one or more patient locations are within a specified range of the clinician location, the automatically determining comprising:

locating a junction point within the generated data structure that is between the clinician identifier and the patient location, wherein the patient location is a direct child location of the junction point; and after locating the junction point, identifying a first pathway to the junction point from the clinician identifier, identifying a second pathway to the junction point from the patient location, and combining the first pathway and the second pathway for a full pathway;

based on the automatically determining, automatically creating a patient list that includes the one or more patient locations within the specified range of the clinician location clinician; and displaying, on a user interface, the full pathway upon a selection of a patient on the patient list.

2. The computer storage media of claim 1, wherein the method further comprises:

presenting a patient's medical chart in response to the selection on the user interface.

3. The computer storage media of claim 1, wherein within the specified range is a predefined distance or proximity between the clinician location and the patient location or any other individual and/or item associated with an identifier.

4. The computer storage media of claim 1, the method further comprising:

identifying a third pathway to the junction point from the clinician identifier;

determining that the first pathway is a shorter pathway relative to the third pathway; and based on the determining, combining the third pathway and the second pathway for display on the user interface upon the selection.

5. The computer storage media of claim 1, wherein the healthcare environment includes multiple floors and multiple elevators, and wherein the data structure represents a single floor of the multiple floors of the healthcare environment.

6. One or more computer storage media having computer-useable instructions embodied thereon that, when used by one or more computing devices, cause the one or more computing devices to perform a method for enhancing healthcare workflows based on pathway-proximity, the method comprising:

receiving destination locations visited by a clinician based on a clinician identifier being tracked via a plurality of sensors in a healthcare environment;

based on the receiving, generating a data structure comprising:

a plurality of paths comprising at least two sub paths and a common path, wherein the plurality of paths are associated with the destination locations and the clinician identifier; and a plurality of locations comprising the destination locations, a clinician location provided by the clinician identifier, and junction points;

based on the receiving, automatically determining a full pathway to a predetermined destination location, the automatically determining comprising:

locating a junction point within the generated data structure that is between the clinician identifier and the destination location; and after locating the junction point, identifying a first pathway to the junction point from the clinician identifier, identifying a second pathway to the junction point from the destination location, and combining the first pathway and the second pathway for the full pathway;

based on the automatically determining, automatically creating a list that includes one or more destination locations; and displaying, on a user interface, the full pathway upon a selection of one of the one or more destination locations on the list.

7. The computer storage media of claim 6, wherein the plurality of sensors utilize one of ultrasound technology, infrared technology, or radio-frequency identification technology.

8. The computer storage media of claim 6, wherein the healthcare environment includes multiple floors and multiple elevators.

9. A system useful in a computer healthcare system enhancing healthcare workflows based on pathway-proximity, the system comprising:
one or more processing devices configured to:
(1) receive a clinician location by way of a clinician identifier in a healthcare facility;
(2) automatically identify a patient location within a specified pathway-proximity to the clinician location in the healthcare facility;
(3) based at least on analyzing a data structure that represents a portion of the healthcare facility, automatically providing a full pathway for a clinician by:
locating a common intersection, within the data structure, that is between the clinician location and the patient location; and
after locating the common intersection, identifying a first pathway and a second pathway, and combining the first pathway and the second pathway for the full pathway; and
(4) automatically load the full pathway onto a user interface.

10. The system of claim 9, wherein the clinician identifier is tracked via a plurality of sensors in the healthcare facility.

11. The system of claim 10, wherein the plurality of sensors utilize one of ultrasound technology, infrared technology, or radio-frequency identification technology.

12. The system of claim 9, wherein the patient location is determined based on a patient identifier that is identified by a plurality of sensors in the healthcare facility.

13. The system of claim 9, wherein the healthcare facility includes multiple floors and multiple elevators.

14. The computer storage media of claim 1, wherein the first pathway comprises a third pathway and a fourth pathway, the third pathway from the clinician identifier to a common junction point and the fourth pathway from the common junction point to the junction point.

15. The computer storage media of claim 1, wherein the specified range is within a particular wing of the healthcare environment.

16. The computer storage media of claim 6, wherein the predetermined destination locations were determined based on which clinician in the healthcare environment had a shortest pathway-proximity to the destination location.

17. The computer storage media of claim 6, wherein the predetermined destination locations were determined based on how many times the clinician visited the destination location.

18. The system of claim 9, wherein the first pathway and the second pathway are located on a same path.

19. The system of claim 9, the automatically providing further comprising identifying a third pathway and combining the first pathway, the second pathway, and the third pathway for the full pathway, wherein the first pathway is from the clinician location to a first closest intersection relative to the clinician location, wherein the second pathway is from the patient location to a second closest intersection relative to the patient location, and wherein the third pathway is from the first closest intersection to the second closest intersection.

20. The system of claim 9, the automatically providing further comprising:
determining whether the patient location is a direct child of the common intersection;
if not the direct child, then locating an additional intersection that is between the clinician location and the patient location and determining whether the patient location is the direct child of the additional intersection, and repeating until the patient location is the direct child; and
identifying additional pathways to combine for the full pathway.

* * * * *

UNITED STATES PATENT AND TRADEMARK OFFICE
CERTIFICATE OF CORRECTION

PATENT NO. : 10,748,653 B2
APPLICATION NO. : 14/961080
DATED : August 18, 2020
INVENTOR(S) : Aaron Timothy Diffenderfer Page 1 of 1

It is certified that error appears in the above-identified patent and that said Letters Patent is hereby corrected as shown below:

In the Claims

Column 18, Line 02: Please remove "clinician location clinician" and replace with --clinician location--.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*